United States Patent
Nishimura et al.

(10) Patent No.: US 10,125,142 B2
(45) Date of Patent: Nov. 13, 2018

(54) METHOD FOR PURIFYING MITOMYCIN C

(71) Applicant: Kyowa Hakko Kirin Co., Ltd., Tokyo (JP)

(72) Inventors: Koichiro Nishimura, Tokyo (JP); Masahiro Hoshikawa, Tokyo (JP); Shuji Ishihara, Tokyo (JP); Takashi Mimura, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 15/579,230

(22) PCT Filed: Jun. 3, 2016

(86) PCT No.: PCT/JP2016/066540
§ 371 (c)(1),
(2) Date: Dec. 4, 2017

(87) PCT Pub. No.: WO2016/195059
PCT Pub. Date: Dec. 8, 2016

(65) Prior Publication Data
US 2018/0179219 A1 Jun. 28, 2018

(30) Foreign Application Priority Data
Jun. 5, 2015 (JP) .................................. 2015-114495

(51) Int. Cl.
*C07D 487/14* (2006.01)
*B01D 9/00* (2006.01)

(52) U.S. Cl.
CPC ........... *C07D 487/14* (2013.01); *B01D 9/005* (2013.01); *B01D 2009/0086* (2013.01)

(58) Field of Classification Search
CPC ............................. C07D 487/14; B01D 9/005
See application file for complete search history.

(56) References Cited

FOREIGN PATENT DOCUMENTS

| JP | 35-17897 | 12/1960 |
|---|---|---|
| JP | 36-9094 | 6/1961 |
| JP | 04-187092 | 7/1992 |
| JP | 2001-31680 | 2/2001 |

OTHER PUBLICATIONS

English translation of Seihin Kikakusho Methanol Wako Ikkyu, Wako Pure Chemical Industries, Ltd. [online], 2006, [retrieval date Aug. 5, 2016 (Aug. 5, 2016)], Internet: <URL:http://www.siyaku.com/uh/Sks.do?pcode=13-0183&now=1470633046137&JE=J&pop_zenkai gst=1>, entire text, previously cited in an IDS filed on Dec. 1, 2017.
Partial English Translation of Hideyuki Azuma, "ICH Guideline Q3D (Kinzoku Fujunbutsu) ni Taio suru Iyakuhin To no Kinzoku Fujunbutsu Bunseki", SCAS News, 2014, vol. 40, pp. 11 to 14, previously cited in an IDS filed on Dec. 1, 2017.
English translation of Seihin Kikakusho Methanol SC, Wako Pure Chemical Industries, Ltd. [online], 2011, [retrieval date Aug. 5, 2016 (Aug. 5, 2016)], Internet: <URL: http://www.siyaku.com/uh/Sks.do?pcode=13-1639&now=1470632958914&JE=J&pop_zenkai gst=1>, entire text, previously cited in an IDS filed on Dec. 1, 2017.
Machine translation of JP 35-17897 previously cited in an IDS filed on Dec. 1, 2017.
Machine Translation of JP 36-9094 previously cited in an IDS filed on Dec. 1, 2017.
International Search Report dated Aug. 23, 2016 in International Application No. PCT/JP2016/066540.
Iyengar, Bhashyam s. et al., Journal of Medicinal Chemistry, 1986, vol. 29, No. 1, pp. 144-147, ISSN 0022-2623, particularly, p. 144, left column, lines 6-11, p. 144, right column, line 8-p. 145, left column, line 14.
Seihin Kikakusho Methanol Wako Ikkyu, Wako Pure Chemical Industries, Ltd. [online], 2006, [retrieval date Aug. 5, 2016 (Aug. 5, 2016)], Internet: <URL:http://www.siyaku.com/uh/Sks.do?pcode=13-0183&now=1470633046137&JE=J&pop_zenkai gst=1>, entire text.
Hideyuki Azuma, "ICH Guideline Q3D (Kinzoku Fujunbutsu) ni Taio suru Iyakuhin To no Kinzoku Fujunbutsu Bunseki", SCAS News, 2014, vol. 40, pp. 11 to 14.
Seihin Kikakusho Methanol SC, Wako Pure Chemical Industries, Ltd. [online], 2011, [retrieval date Aug. 5, 2016 (Aug. 5, 2016)], Internet: <URL:http://www.siyaku.com/uh/Sks.do?pcode=13-1639&now=1470632958914&JE=J&pop_zenkai gst=1>, entire text.

*Primary Examiner* — Golam M Shameem
(74) *Attorney, Agent, or Firm* — Wenderoth, Lind & Ponack, L.L.P.

(57) ABSTRACT

Provided are a method for purifying mitomycin C, comprising a step of recrystallizing crude mitomycin C crystals using a high-purity methanol; mitomycin C obtainable by the method; and the like.

7 Claims, No Drawings

METHOD FOR PURIFYING MITOMYCIN C

TECHNICAL FIELD

The present invention relates to a method for purifying mitomycin C; and the like.

BACKGROUND ART

Mitomycin C is an antitumor antibiotic which can be obtained by culturing a strain of Streptomyces caespitosus and is widely used clinically.

Various methods for purifying mitomycin C from the culture medium harvested after the culture of the above-mentioned bacterial strain are conventionally known. For example, included are an activated carbon adsorption method which comprises adding activated carbon to the culture supernatant separated from the bacterial cells by filtration to allow mitomycin C to adsorb thereto, followed by eluting mitomycin C with an organic solvent; and a method which comprises transferring mitomycin C in the culture supernatant to an organic phase, concentrating the organic phase, purifying the mitomycin C-containing concentrate by alumina chromatography or counter current distribution, concentrating the mitomycin C-containing eluate to dryness, and adding a small amount of acetone to the resulting solid to give crystals (Patent Literature 1).

Another known method comprises allowing mitomycin C in the culture medium to adsorb to a reverse-phase adsorption resin; eluting mitomycin C with a solvent such as acetone, methanol and ethanol; concentrating the eluate to remove the solvent, followed by sodium chloride saturation and phase transfer to chloroform; subjecting the chloroform extract to alumina column chromatography for separation and elution of mitomycin C; concentrating the eluate into a dense solution of mitomycin C in methanol, followed by adding ether, petroleum ether, benzine or ligroine to this solution to give pure mitomycin C crystals; concentrating the mother liquor as well, followed by repeating the same procedure as above to give crude crystals; and washing the crude crystals with a mixture of 10% methanol and ether to give pure mitomycin C crystals (Patent Literature 2).

Yet another known method comprises allowing mitomycin C in the culture medium to adsorb to a reverse-phase adsorption resin; eluting mitomycin C with ethyl acetate; evaporating off the solvent in the eluate; allowing mitomycin C in the residue to adsorb to a reverse-phase adsorbent with a small particle size; eluting mitomycin C with hydrous methanol; allowing mitomycin C in the eluate to adsorb to a reverse-phase adsorption resin; eluting mitomycin C from the resin with methanol; and concentrating the eluate to crystallize mitomycin C (Patent literature 3).

Also known is a method which uses a solvent system consisting of a combination of a mitomycin C-soluble solvent and a poor solvent for the production of mitomycin C crystals (Patent Literature 4).

CITATION LIST

Patent Literature

Patent Literature 1: JP-B 35-17897
Patent Literature 2: JP-B 36-9094
Patent Literature 3: JP-A 4-187092
Patent Literature 4: JP-A 2001-31680

SUMMARY OF INVENTION

Technical Problem

Regarding mitomycin C for injections and mitomycin C injections, there was a case where the number of insoluble particles derived frost mitomycin C increased rapidly, resulting in mitomycin C injections deviating from the requirements for injections; "the number of particles having a diameter of 10 µm or more does not exceed 6000 per container and the number of particles having a diameter of 25 µm or more does not exceed 600 per container" (The Japanese Pharmacopoeia, 16th edition—Insoluble Particulate Matter Test for Injections). Therefore, there has been a need for improvement of the purification methods of crude mitomycin C crystals in the production of mitomycin C for injections and mitomycin C injections.

An object of the present invention is to provide a method for purifying mitomycin C to enable the production of mitomycin C which is less prone to a time-dependent increase in insoluble particulate matter; and the like.

Solution to Problem

The present inventors conducted extensive research to solve the above-described problem. As a result, the present inventors found that the use of a high-purity methanol in purifying crude mitomycin C crystals enables stable production of mitomycin C which is less prone to a time-dependent increase in insoluble particulate matter.

The present invention relates to, for example, the following (1) to (23).

(1) A method for purifying mitomycin C, comprising a step of recrystallizing crude mitomycin C crystals using a high-purity methanol.

(2) The method according to the above (1), wherein the high-purity methanol has a purity of 99.00 to 99.99%.

(3) The method according to the above (1), wherein the high-purity methanol has a purity of 99.50 to 99.99%.

(4) The method according to any one of the above (1) to (3), wherein the high-purity methanol has a total metal concentration of 0.01 to 300 ppb.

(5) The method according to any one of the above (1) to (3), wherein the high-purity methanol has a total metal concentration of 0.01 to 100 ppb.

(6) The method according to any one of the above (1) to (3), wherein the high-purity methanol has a zinc concentration of 0.01 to 100 ppb.

(7) The method according to any one of the above (1) to (3), wherein the high-purity methanol has a zinc concentration of 0.01 to 10 ppb.

(8) Mitomycin C obtainable by the method according to any one; of the above (1) to (7).

(9) A method for reducing insoluble particle formation, comprising a step of recrystallizing crude mitomycin C crystals using a high-purity methanol.

(10) The method according to the above (9), wherein the high-purity methanol has a purity of 99.00 to 99.99%.,

(11) The method according to the above (9), wherein the high-purity methanol has a purity of 99.50 to 99.99%.

(12) The method according to any one of the above (9) to (11), wherein the high-purity methanol has a total metal concentration of 0.01 to 300 ppb.

(13) The method according to any one of the above (9) to (11), wherein the high-purity methanol has a total metal concentration of 0.01 to 100 ppb.

(14) The method according to any one of the above (9) to (11), wherein the high-purity methanol has a zinc concentration of 0.01 to 100 ppb.
(15) The method according to any one of the above (9) to (11), wherein the high-purity methanol has a zinc concentration of 0.01 to 10 ppb.
(16) A method for purifying crude mitomycin C crystals, comprising the following steps (A) to (E):
(A) adding a high-purity methanol to the crude mitomycin C crystals for dissolution;
(B) cooling a filtrate obtained in the above (A);
(C) adding a poor solvent to a solution obtained in the above (B);
(D) filtering a mixture obtained in the above (C) to harvest crystals; and
(E) drying the crystals obtained in the above (D).
(17) The method according to the above (16), wherein the high-purity methanol has a purity of 99.00 to 99.99%.
(18) The method according to the above (16), wherein the high-purity methanol has a purity of 99.50 to 99.99%.
(19) The method according to the above (16), wherein the high-purity methanol has a total metal concentration of 0.01 to 300 ppb.
(20) The method according to the above (16), wherein the high-purity methanol has a total metal concentration of 0.01 to 100 ppb.
(21) The method according to the above (16), wherein the high-purity methanol has a zinc concentration of 0.01 to 100 ppb.
(22) The method according to the above (16), wherein the high-purity methanol has a zinc concentration of 0.01 to 10 ppb,
(23) Mitomycin C obtainable by the method according to any one of the above (16) to (22).

ADVANTAGEOUS EFFECTS OF INVENTION

The present invention provides a method for purifying mitomycin C; mitomycin C which is obtainable by the method and less prone to a time-dependent increase in insoluble particulate matter; and the like.

DESCRIPTION OF EMBODIMENTS

The method of the present invention for purifying crude mitomycin C crystals is described in detail.

The crude mitomycin C crystals used in the present invention can be obtained by, for example, the methods described in JP-B 35-17897, JP-B 36-9094, JP-A 4-187092, etc. Specifically, the crude mitomycin C crystals can be obtained by subjecting the culture medium harvested after the culture of microorganisms to a treatment such as purification by adsorption to activated carbon or resin (e.g., reverse-phase adsorption resin etc.), alumina chromatography and countercurrent distribution; and shall meet the following requirements:
i) the identification test is passed;
ii) the mitomycin C content in 1 mg of the crude mitomycin C crystals is 950 μg or more as measured based on 1 mg of a mitomycin C standard; and
iii) the loss on drying is 1.0% or lower.

The identification test and the measurement of the content and the loss on drying can be performed according to, for example, the methods described in the sections under the heading "Identification", "Assay" and "Loss on drying" of "Mitomycin C" in the Japanese Pharmacopoeia, 16th edition.

The unit v/w in the present invention represents the volume (mL) of a liquid per gram of a substance.

Examples of the poor solvent in the present invention include ethyl ether, petroleum ether and the like.

Examples of the metal in the present invention include organometallic compounds, elemental metals, metal salts and the like. Examples of the elemental metal include: nickel, lead, cadmium, iron, zinc and the like. Examples of the metal salt include nickel salts such as nickel chloride, nickel oxide and the like; lead salts such as lead chloride, lead oxide and the like; cadmium salts such as cadmium chloride, cadmium oxide and the like; iron salts such as iron chloride, iron oxide and the like; and zinc salts such as zinc chloride, zinc oxide and the like.

The total metal concentration represents the sum of the content of all the metals detected:, for example;, as the respective metal ions by the metal analysis methods described in Inductively Coupled Plasma Atomic Emission Spectroscopy and Inductively Coupled Plasma Mass Spectrometry <2.63> in the Japanese Pharmacopoeia, 16th edition, and the like, Examples of the zinc in the present invention include organozinc compounds, metal zince, zinc salts and the like. Examples of the zinc salt include zinc chloride, zinc oxide and the like.

Production Method

To the crude mitomycin C crystals, 50 to 100 v/w, preferably 60 to 70 v/w of methanol is added, and the mixture is stirred at a temperature between 50 and 70° C., preferably between 55 and 67° C. for dissolution.

If desired, the resulting solution can be filtered to remove insoluble matter etc.

Examples of the methanol include a methanol having a low total metal concentration; and the like. Examples of the methanol having a low total metal concentration include distilled methanol prepared from a commercial methanol; a commercial high-purity methanol having a low total metal concentration; and the like.

The commercial high-purity methanol having a low total metal concentration is, for example, a commercial purified methanol (manufactured by Toyo Gosei Co., Ltd.) or the like.

The purity of the methanol is, for example, 99.00 to 99.99%, preferably 99.50 to 99.9941 more preferably 99.60 to 99.99%, and particularly preferably 99.80 to 99.99%. The total metal concentration in the methanol is preferably as low as possible. The total metal concentration is, for example, 0.01 to 300 ppb, preferably 0.01 to 100 ppb, more preferably 0.01 to 30 ppb, and particularly preferably 0.01 to 10 ppb. The zinc concentration in the methanol is preferably as low as possible. The zinc concentration is, for example, 0.01 to 100 ppb, preferably 0.01 to 10 ppb, more preferably 0101 to 7 ppb, and particularly preferably 0.01 to 6 ppb.

The solution obtained above or the filtrate obtained above by filtration of the solution is cooled, 70 to 110 v/w, preferably 85 to 95 v/w of ethyl ether relative to the amount of the crude crystals is added, and 200 to 250 v/w, preferably 220 to 230 v/w of petroleum ether relative to the amount of the crude crystals is further added. The resulting mixture is allowed to stand with or without stirring at −10 to 15° C., preferably −5 to 10° C., for 0.5 to 2 hours, preferably 0.8 to 1.2 hours. The precipitated mitomycin C crystals are collected by filtration and dried to give a purified mitomycin C.

Hereinafter, the present invention will he illustrated in more detail by examples, but the present invention is not limited thereto.

EXAMPLE 1

To crude mitomycin C crystals (1.8 g), distilled methanol (117 mL) which had been prepared from a commercial methanol (Wako Pure Chemical Industries, Ltd., first grade) was added, and the mixture was heated at an outside temperature of 65° C. with stirring for 30 minutes. The resulting solution was filtered through a membrane filter with a pore size of 0.22 μm, and the filtrate was harvested. The filtrate was gradually cooled down to 2° C., and then kept at this temperature for 2 hours. To the filtrate, ethyl ether (160 mL) cooled to −10° C. was added dropwise, and then petroleum ether (400 mL) cooled to −7° C. was added dropwise. After 1-hour aging at −2° C., the resulting crystals were collected by filtration under reduced pressure and then dried at room temperature under reduced pressure to give mitomycin C (1.61 g).

COMPARATIVE EXAMPLE 1

Mitomycin C (1.51 g) was obtained, using crude Mitomycin C crystals (1.8 g) and the commercial methanol (Wako Pure Chemical Industries, Ltd., first grade), in the same manner as in Example 1.

COMPARATIVE EXAMPLE 2

Mitomycin C (1.56 g) was obtained, using crude mitomycin C crystals (1.8 g) and 5-fold concentrated methanol prepared from the commercial methanol (Wako Pure Chemical Industries, Ltd., first grade) with a rotary evaporator, in the same manner as in Example 1.

TEST EXAMPLE 1

Quantification of Zinc in Methanol and Mitomycin C
1) Methanol
500 mL of methanol was charged into an eggplant-shaped flask and concentrated to dryness with an evaporator. The eggplant-shaped flask was washed out with a 4% aqueous nitric acid solution prepared by dilution of special-grade nitric acid (Wako Pure Chemical. Industries, Ltd.), and the washout solution (final volume: 50 mL) was harvested and used as a sample solution.
2) Mitomycin C
0.2 g of each mitomycin C prepared in the above Example 1 and Comparative Examples 1 and 2 was separately weighed out in a vessel. To the vessel, 3 mL of special-grade nitric acid (Wako Pure Chemical Industries, Ltd.) and 3 mL of special-grade hydrogen peroxide solution (Junsei Chemical Go., Ltd.) were added, and water was added to make up the volume to 50 mL exactly. The resulting solution was used as a sample solution.

The sample solutions were tested according to the calibration curve method of inductively coupled plasma atomic emission spectroscopy (<2.63> in the Japanese Pharmacopoeia) under the following conditions.
Test conditions
Wavelength; 213.856 nm for zinc
High frequency power: 1.2 kW
Carrier gas: Argon
Carrier gas flow rate; 0.7 L/min
Auxiliary gas flow rate: 0.6 L/min
Coolant gas flow rate: 10.0 L/min
The measured concentration of zinc in each methanol used for the purification of the crude mitomycin C crystals in the above Example 1 and Comparative Examples 1 and 2 is shown in Table 1.

TABLE 1

Zinc concentration in solvents

|  | Methanol used | Zinc concentration in methanol (ppb) |
|---|---|---|
| Example 1 | Distilled product | 0 |
| Comparative Example 1 | Commercial product | 628 |
| Comparative Example 2 | Concentrated product | 2549 |

*The quantitative limit is 1.26 ppb.

The measured concentration of zinc in each mitomycin C purified in the above Example 1 and Comparative Examples 1 and 2 is shown in Table 2.

TABLE 2

Zinc concentration in mitomycin C

|  | Zinc concentration (ppb) |
|---|---|
| Example 1 | 2223 |
| Comparative Example 1 | 30394 |
| Comparative Example 2 | 120337 |

The quantitative limit is 1250 ppb.

The number of particles formed during the storage of each mitomycin C purified in Example 1 and Comparative Examples 1 and 2 was examined according to the method described in the following Test Example 2.

TEST EXAMPLE 2

Change in the Number of Particles in Mitomycin C in a Stability Test under Severe Conditions 300 mg of each mitomycin C prepared in Example 1 and Comparative Examples 1 and 2 is separately placed into a vial, and stored at 50° C. under uncontrolled humidity. Sampling was performed after 0, 191 and 300 hours from the onset of the storage, and whether the number of particles would increase was examined according to the following section "Quantification of Particles in Mitomycin C".
Quantification of Particles in Mitomycin C 10 mg of mitomycin C was weighed out accurately, water for injection was added to make up the volume to 25 mL exactly, and the resulting solution was used as a sample solution.

The particles in mitomycin C were analyzed with MFI DPA5200 (Protein Simple). Prior to the analysis of the sample solution, the passage in the analytical device was washed with water for injection to obtain the particle-free baseline. 1 mL of the sample solution was drawn into a pipette tip and then loaded on the sample holder. The sample solution was allowed to pass into the passage at a flow rate 0.1 mL/min to completely replace the liquid in the passage, and then the analysis of the sample; solution was started (volume for analysis: 0.61 mL).

The obtained data was filtered on MVAS 1.3 software to extract particles having an aspect ratio of less than 0.85 for the purpose of excluding bubbles. The number of particles having a diameter of 10 μm or more in 10 mg of mitomycin C and the number of particles having a diameter of 25 μm or more in 10 mg of mitomycin C were separately counted using Microsoft Excel.

The above procedure was repeated 3 times, and the average value of the triplicates was used as the quantitative value.

TABLE 3

Time-dependent change in number of particles in 10 mg of mitomycin C under severe conditions

|  | Initial | | 191 hours | | 300 hours | |
| --- | --- | --- | --- | --- | --- | --- |
|  | ≥10 μm | ≥25 μm | ≥10 μm | ≥25 μm | ≥10 μm | ≥25 μm |
| Example 1 | 3047 | 151 | 3624 | 273 | 5683 | 314 |
| Comparative Example 1 | 2118 | 246 | 7063 | 861 | 22527 | 3005 |
| Comparative Example 2 | 3853 | 178 | 279617 | 51953 | 301967 | 36216 |

The results snow that the mitomycin C prepared in Example 1 showed almost no increase in either the number of particles having a diameter of 10 μm or more or the number of particles having a diameter of 25 μm or more even after 300-hour exposure to severe conditions. In contrast, the mitomycin C prepared in Comparative Example 1 or 2, which contained a larger amount of zinc than that in Example 1, showed a significant increase in both the number of particles having a diameter of 10 μm or more and the number of particles having a diameter of 25 μm or more after 300-hour exposure to severe conditions.

Therefore, from the test results, it was found that the reduction of the zinc concentration in mitomycin C is effective for the reduction of the time-dependent increase in insoluble particulate matter in mitomycin C. To this end, the reduction of the residual, zinc concentration in mitomycin C by the mitomycin C purification method of the present invention using a high-purity methanol is considered effective.

INDUSTRIAL APPLICABILITY

The present invention provides a method for purifying mitomycin C; and the like.

The invention claimed is:

1. A method for purifying mitomycin C, comprising a step of recrystallizing crude mitomycin C crystals using a high-purity methanol.

2. The method according to claim 1, wherein the high-purity methanol has a purity of 99.00 to 99.99%.

3. The method according to claim 1, wherein the high-purity methanol has a purity of 99.50 to 99.99%.

4. The method according to claim 1, wherein the high-purity methanol has a total metal concentration of 0.01 to 300 ppb.

5. The method according to claim 1, wherein the high-purity methanol has a total metal concentration of 0.01 to 100 ppb.

6. The method according to claim 1, wherein the high-purity methanol has a zinc concentration of 0.01 to 100 ppb.

7. The method according to claim 1, wherein the high-purity methanol has a zinc concentration of 0.01 to 10 ppb.

* * * * *